(12) United States Patent
Dou et al.

(10) Patent No.: US 10,466,159 B2
(45) Date of Patent: Nov. 5, 2019

(54) MULTIPLEX BEAD ARRAY ASSAY

(71) Applicant: ChipCare Corporation, Toronto (CA)

(72) Inventors: James Jiahua Dou, Oakville (CA); Lu Chen, Thornhill (CA); James Andrew Fraser, Toronto (CA); Rakesh Kumar Nayyar, Thornhill (CA)

(73) Assignee: ChipCare Corporation, Toronto, ON, CA (US)

( * ) Notice: Subject to any disclaimer, the term of this patent is extended or adjusted under 35 U.S.C. 154(b) by 0 days.

(21) Appl. No.: 15/531,397

(22) PCT Filed: Nov. 25, 2015

(86) PCT No.: PCT/IB2015/002460
§ 371 (c)(1),
(2) Date: May 26, 2017

(87) PCT Pub. No.: WO2016/083898
PCT Pub. Date: Jun. 2, 2016

(65) Prior Publication Data
US 2017/0343466 A1 Nov. 30, 2017

Related U.S. Application Data

(60) Provisional application No. 62/085,441, filed on Nov. 28, 2014.

(51) Int. Cl.
*C12Q 1/6825* (2018.01)
*C12Q 1/6837* (2018.01)
(Continued)

(52) U.S. Cl.
CPC ......... *G01N 15/1463* (2013.01); *A61B 5/151* (2013.01); *B01L 3/502761* (2013.01);
(Continued)

(58) Field of Classification Search
None
See application file for complete search history.

(56) References Cited

U.S. PATENT DOCUMENTS 6,382,254 B1 5/2002 Yang et al.
8,609,336 B2 12/2013 Dahlberg et al.
(Continued)

FOREIGN PATENT DOCUMENTS

DE 102008021364 A1 6/2009
EP 0733714 A2 9/1996
(Continued)

OTHER PUBLICATIONS

Sasso et al. Microfluid Nanofluidcs. 2012. 13(4):603-612. (Year: 2012).*
(Continued)

*Primary Examiner* — Joseph G. Dauner
(74) *Attorney, Agent, or Firm* — Wilson Sonsini Goodrich & Rosati

(57) ABSTRACT

The present disclosure relates to a system, method, and kit for particle detection and analysis. Devices disclosed herein may include at least an optical source, a fluidic chip containing a multiplex bead array, and a detection module, wherein the sample flows within the fluidic chip past a detection window, where the cells or particles are imaged by an image acquisition and analysis module that may include an optical detector. The image acquisition and analysis module counts the labeled particles and software allows for analysis of bead population.

12 Claims, 4 Drawing Sheets

(51) Int. Cl.

| | | |
|---|---|---|
| *G01N 15/14* | (2006.01) | |
| *G01N 15/06* | (2006.01) | |
| *G01N 33/543* | (2006.01) | |
| *A61B 5/151* | (2006.01) | |
| *B01L 3/00* | (2006.01) | |
| *G01N 21/64* | (2006.01) | |
| *G01N 15/10* | (2006.01) | |
| *G16H 50/20* | (2018.01) | |
| *G01N 15/00* | (2006.01) | |
| *G06F 19/00* | (2018.01) | |
| *G08B 21/18* | (2006.01) | |

(52) U.S. Cl.
CPC ......... *C12Q 1/6825* (2013.01); *C12Q 1/6837* (2013.01); *G01N 15/06* (2013.01); *G01N 15/147* (2013.01); *G01N 15/1459* (2013.01); *G01N 15/1484* (2013.01); *G01N 21/6428* (2013.01); *G01N 33/54313* (2013.01); *G01N 33/54326* (2013.01); *G01N 33/54366* (2013.01); *B01L 2200/0647* (2013.01); *B01L 2200/10* (2013.01); *B01L 2200/16* (2013.01); *B01L 2200/18* (2013.01); *B01L 2300/023* (2013.01); *B01L 2300/024* (2013.01); *B01L 2300/025* (2013.01); *B01L 2300/0654* (2013.01); *B01L 2300/0816* (2013.01); *G01N 2015/0065* (2013.01); *G01N 2015/0693* (2013.01); *G01N 2015/1006* (2013.01); *G01N 2015/1486* (2013.01); *G01N 2021/6439* (2013.01); *G01N 2458/00* (2013.01); *G06F 19/321* (2013.01); *G06F 19/328* (2013.01); *G08B 21/18* (2013.01); *G16H 50/20* (2018.01)

(56) References Cited

U.S. PATENT DOCUMENTS

| | | | |
|---|---|---|---|
| 2001/0041333 A1 | 11/2001 | Short et al. | |
| 2002/0051971 A1* | 5/2002 | Stuelpnagel | B01L 3/5027 435/6.11 |
| 2004/0132122 A1* | 7/2004 | Banerjee | B01J 19/0046 435/7.92 |
| 2006/0134774 A1* | 6/2006 | Clausen | C12Q 1/37 435/287.2 |
| 2007/0086918 A1 | 4/2007 | Hartley et al. | |
| 2008/0176242 A1* | 7/2008 | McMaster | C12Q 1/682 435/6.12 |
| 2009/0042737 A1 | 2/2009 | Katz et al. | |
| 2009/0081773 A1 | 3/2009 | Kaufman | |
| 2010/0267049 A1 | 10/2010 | Rutter et al. | |
| 2010/0291584 A1 | 11/2010 | Tseng et al. | |
| 2012/0177543 A1 | 7/2012 | Battrell et al. | |
| 2014/0170679 A1 | 6/2014 | Aitchison et al. | |
| 2014/0274778 A1 | 9/2014 | Tsao et al. | |
| 2017/0218425 A1 | 8/2017 | Chen et al. | |

FOREIGN PATENT DOCUMENTS

| | | | |
|---|---|---|---|
| EP | 1418233 A1 | 5/2004 | |
| EP | 2437890 A1 | 4/2012 | |
| EP | 3201311 A1 | 8/2017 | |
| EP | 3224594 A1 | 10/2017 | |
| WO | WO-2005066368 A2 | 7/2005 | |
| WO | WO-2005106024 A1 | 11/2005 | |
| WO | WO-2007133710 A2 | 11/2007 | |
| WO | WO-2009063379 A1 | 5/2009 | |
| WO | WO-2010115167 A2 | 10/2010 | |
| WO | WO-2012119243 A2 | 9/2012 | |
| WO | WO-2012154306 A1 | 11/2012 | |
| WO | WO-2015001070 A1 | 1/2015 | |
| WO | WO-2016051272 A1 | 4/2016 | |
| WO | WO-2016083898 A1 | 6/2016 | |

OTHER PUBLICATIONS

Anonymous, BD Cytometric Bead Array: Multiplexed Bead-Based Immunoassays. pp. 1-14, 2012. [retrieved on Mar. 31, 2016]. Retrieved from the Internet<URL: https://www.bdbiosciences.com/documents/CBA_Brochure_Intl.pdf>.

Kuo et al., Deformability consideration in filtration of biological cells. Lab On A Chip, 10(7):837-842, 2010.

Li, Paul et al., Imaging for degradation of ikB-EGFP in a single Jurkat T cell studied within a microfluidic channel. 7th International Conference on Miniaturized Chemical and Biochemical Analysis Systems, Squaw Valley, CA, p. 1149-1152, Oct. 5-9, 2003.

PCT/CA2012/000227 International Preliminary Report on Patentability dated Jul. 17, 2013.

PCT/CA2012/000227 International Search Report and Written Opinion dated Oct. 17, 2012.

PCT/EP2014/064290 International Preliminary Report on Patentability dated Jan. 5, 2016.

PCT/EP2014/064290 International Search Report and Written Opinion dated Sep. 29, 2014.

PCT/IB2015/002084 International Preliminary Report on Patentability dated Apr. 13, 2017.

PCT/IB2015/002084 International Search Report and Written Opinion dated Feb. 22, 2016.

PCT/IB2015/002460 International Preliminary Report on Patentability dated May 30, 2017.

PCT/IB2015/002460 International Search Report and Written Opinion dated Sep. 29, 2014.

Taylor et al., Dynamic analysis of MARK signaling using a high-throughput microfluidic single-cell imaging platform. PNAS, 105(10):3758-3763, 2009.

Vostry, Multiplex immunoassays: Chips and beads. Journal of the International Federation of Clinical Chemistry and Laboratory Medicine. 20(4):4 pages, 2009.

Zhao et al., Method for the accurate preparation of cell-spiking standards. Anal. Chem., 81(3):1285-1290, 2009.

Braeckmans, et al. Encoding Microcarriers: Present and Future Technologies. Nature Reviews Drug Discovery. 2002; 1:447-456.

Dunbar et al. Introduction to Luminex? xMAP? Technology and Applications for Biological Analysis in China. Asiobiotec 14(10):26-30 (2010).

European Patent Application No. 15847832.1 Extended Search Report dated May 24, 2018.

European Patent Application No. 15862356.1 Extended Search Report dated Jul. 5, 2018.

Nguyen et al. MEMS-Micropumps: A Review. J Fluids Eng 124(2):384-392 (2002).

Sheybani et al. A MEMS electrochemical bellows actuator for fluid metering applications. Biomedical Microdevices 15(1):37-48:1-28 (2013).

U.S. Appl. No. 15/515,517 Office Action dated Sep. 10, 2018.

Yager et al. Microfluidic diagnostic technologies for global public health. Nature 442:412-418 (2006).

Chinese Patent Application No. 2015800748231 First Office Action dated May 22, 2019.

Yager et al.: Microfluidic diagnostic technologies for global public health; Nature Publishing Group; vol. 442, pp. 412-418 (2006).

U.S. Appl. No. 15/515,517 Final Office Action dated Jan. 17, 2019.

\* cited by examiner

MULTIPLEX BEAD ARRAY ASSAY

CROSS REFERENCE

This application is a National Stage Entry of PCT/IB2015/002460, filed on Nov. 25, 2015, which claims the benefit of U.S. Application No. 62/085,441, filed Nov. 28, 2014, both of which are incorporated by reference in their entirety.

BACKGROUND OF THE INVENTION

Detection and quantification of antigens, analytes or other microparticulates is important in diagnosing and treating many conditions that impair human health. For example, identifying CD4 T-cell counts in patients provide physicians with information of the patient's HIV infection status. Healthcare providers often take multiple CD4 T-cell counts over time in order to determine the progression of the disease and the effectiveness of HIV treatments. A falling CD4 T-cell count indicates that HIV is progressing and damaging the immune system, whereas a rising CD4 T-cell count indicates that HIV treatments are altering the course of the disease.

SUMMARY OF THE INVENTION

Provided herein are systems, detection methods, and kits for assaying multiple antigens, analytes or other microparticulates from patient samples. In one embodiment, provided herein is a system for detecting analytes in a sample comprising: one or more housing units; a bead array, wherein the bead array comprises at least one detection bead labelled with a detectable signal and a capture probe attached to the detection bead surface and wherein the bead array is capable of detecting more than two analytes in a sample; an analyte detection molecule; a fluidic chip, the fluidic chip incorporating at least one microfluidic channel that one or more detection beads flows through within the fluidic chip; a detection window incorporated in one of the one or more housings, the detection window being operable to facilitate the capture of one or more images of one or more detection beads flowing within the detection window; and a detection module, the detection module comprising an optical imaging system and software for image analysis, that allows communication to and from a central database.

In one embodiment, the bead array contains fluorescent detection beads. In some embodiments, the bead array contains detection beads of varying fluorescent wavelengths. In another embodiment, the bead array contains detection beads of varying fluorescent intensities. In yet another embodiment, the bead array contains detection beads of varying sizes. In still other embodiments, the bead array comprises fluorescent beads coupled with a capture probe. In some embodiments, the detection beads have a magnetic microbead core. In other embodiments, the detection beads have a polymer coating. In some embodiments, the detection beads have quantum dots. In other embodiments, the capture probe is an antibody. In still other embodiments, the capture probe is an oligonucleotide probe. In yet other embodiments, the bead array comprises a detection molecule. In still other embodiments, the detection molecule is biotinylated. In some embodiments, the bead array also comprises streptavidin conjugated with phycoerythrin. In some embodiments, all reagents required for the test are supplied and sealed in the cartridge. In still other embodiments, the reagents are dried on the chip. In yet other embodiments, the reagents are lyophilized or slow dried. In other embodiments, the reagents and kits disclosed herein are shelf-stabilized. In yet other embodiments, the reagents and kits disclosed herein are stable for at least 12 months. In still other embodiments, the reagents on the cartridge and kits disclosed herein have a shelf life of at least 12 months at 0° C. to 40° C. In some embodiments, the reagents on the cartridge and kits disclosed herein have a shelf life of at least 48 hours with fluctuations between 0° C. to 50° C.

In some embodiments, the detection module further comprises: an optical imaging system comprising a light source and detector; software for image analysis, that allows communication to and from a central database; a display; an input/output means; CPU; storage or memory means; power control; and communication means. In some embodiments, the detection module is ruggedized. In other embodiments, the detection module is portable. In other embodiments, the detection module comprises a power supply. In still other embodiments, the detection module comprises a rechargeable battery. In yet other embodiments, the detection module comprises a keyboard. In some embodiments, the detection module comprises a touchscreen. In some embodiments, the detection module is readable in dim light conditions. In still other embodiments, the detection module is readable in direct sunlight. In some embodiments, the dimensions of the detection module do not exceed 25×15×5 cm. In some embodiments, the detection module uses visual and audible indicators to communicate to the user when a test is complete or has failed. In other embodiments, the detection module is capable of reading, displaying, and storing a date, time, operator ID, patient ID, site ID, cartridge ID, instrument ID, and quality control status. In some embodiments, the detection module may be disabled by a central data center. In still other embodiments, the software maintains privacy standards equivalent to HIPAA (Health Insurance Portability and Accountability Act (Public Law 104-191 (Aug. 21, 1996)) when displaying, storing, and transmitting patient data. In some other embodiments, the software can be updated or upgraded from a remote server. In yet other embodiments, the detection module can connect to a computer using a USB port. In still other embodiments, the detection module is capable of accepting a replaceable SIM card. In yet other embodiments, the detection module is capable of reading bar codes or accepting information manually entered through a keyboard.

Disclosed herein are methods for assaying at least two antigens, analytes, or other microparticulates, comprising: introducing a sample to a microfluidic chamber on a microfluidic chip; mixing the sample with analyte detection beads, the beads comprising a mixture of beads impregnated with different fluorescent or other light-based signals that allow differentiation of different populations of beads; washing the sample and detection bead mixture; mixing the sample and detection bead mixture with a first detector molecule; washing the sample, detection bead, and detection molecule mixture; mixing the sample and detection bead mixture with a second detector molecule; and detecting the detection beads using a detection module operable to capture one or more images of the one or more cells flowing within the fluidic chip.

In one aspect, disclosed herein is a system for particle detection and analysis comprising: one or more housing units; a multiplex bead array; a fluidic chip incorporating at least one microfluidic channel that one or more detection beads flows through within the fluidic chip; a detection window incorporated in one of the one or more housings, the detection window being operable to facilitate the capture of one or more images of one or more detection beads flowing within the detection window; and a detection module, the detection module comprising an optical imaging system and software for image analysis, that allows communication to and from a central database.

The multiplex bead array utilizes fluorescence for detection and quantification. In some embodiments, the multiplex bead array contains fluorescent detection beads. In some embodiments, the multiplex bead array contains detection beads of varying fluorescent wavelengths. In some embodiments, the multiplex bead array contains detection beads of varying fluorescent intensities. In some embodiments, the multiplex bead array contains detection beads of varying sizes. In some embodiments, the multiplex bead array comprises fluorescent beads coupled with a capture probe. In some embodiments, the capture probe is an antibody. In other embodiments, the capture probe is an oligonucleotide probe. In some embodiments, the detection molecule is biotinylated. In some embodiments, the multiplex bead array also comprises streptavidin conjugated with phycoerythrin.

In some embodiments, the multiplex bead array utilizes detection beads. In some embodiments, the detection beads have a magnetic microbead core. In other embodiments, the detection beads have a polymer coating. In some embodiments, the detection beads have quantum dots.

In some embodiments, all reagents required for the test are supplied and sealed in the cartridge. In further embodiments, the reagents are dried in the cartridge or device. In further embodiments, the reagents are lyophilized. In further embodiments, the reagents on the cartridge have a shelf life of at least 12 months at 0° C. to 40° C., at least 12 months at 10° C. to 40° C., at least 12 months at 10° C. to 30° C., at least 12 months at 20° C. to 30° C., at least 12 months at 10° C., at least 12 months at 20° C., at least 12 months at 30° C., at least 12 months at 40° C. In further embodiments, the reagents on the apparatus have a shelf life of at least 48 hours with fluctuations between 0° C. and 50° C. In some embodiments, the cartridge holds a maximum volume of 50 microliters. In other embodiments, the cartridge holds a maximum volume of 10 microliters to 50 microliters. In yet other embodiments, the cartridge holds a maximum volume of 20 microliters to 40 microliters. In still other embodiments, the cartridge holds a maximum volume of 25 microliters to 30 microliters. In some embodiments, the cartridge requires a minimum of 2 microliters for analysis. In some embodiments the cartridge requires a minimum of 2 microliters to 15 microliters for analysis. In some embodiments, the cartridge requires a minimum of 2 microliters to 10 microliters for analysis. In some embodiments, the cartridge requires a minimum of 2 microliters to 5 microliters for analysis. In some embodiments, the cartridge has a system for metering the amount of blood to be analyzed.

In some embodiments the devices and systems disclosed herein comprises a multi-channel detection module that allows simultaneous detection of multiple fluorescent or other light-based signals. In other embodiments, the devices and systems disclosed herein further comprises: an optical imaging system; software for image analysis, means and devices for allowing communication to and from a central database; a display; an input/output means; CPU; storage or memory means; power control; and communication means. In some embodiments, the detection module further comprises a non-slip gripping surface. In some embodiments, the detection module further comprises a power supply. In further embodiments, the detection module further comprises a rechargeable battery. In further embodiments, the detection module further comprises a keyboard. In some embodiments, the detection module uses visual and audible indicators to communicate to the user when a test is complete or has failed. In some embodiments, the detection module is capable of reading, displaying, and storing a date, time, operator ID, patient ID, site ID, cartridge ID, instrument ID, and quality control status. In some embodiments, the detection module may be disabled by a central data center. In some embodiments, the software maintains privacy standards equivalent to government regulatory standards, for example HIPAA, when displaying, storing, and transmitting patient data. In some embodiments, the detection module's software can be updated or upgraded from a remote server. In some embodiments, the detection module can connect to a computer using a USB port. In some embodiments, the detection module is capable of accepting a replaceable SIM card. In some embodiments, the detection module is capable of reading bar codes or accepting information manually entered through a keyboard.

In another aspect, disclosed herein are assay methods for detecting one or more analytes, antigens, or other microparticles in a sample, comprising: introducing a sample to a microfluidic chamber on a microfluidic chip; mixing the sample with labeled detection beads conjugated to a capture probe, the beads comprising a mixture of beads impregnated with different fluorescent or other light-based signals that allow differentiation of different populations of beads; washing the sample and detection bead mixture; mixing the sample and detection bead mixture with the detection molecule; washing the sample, detection bead, and detection molecule mixture; detecting and quantifying the detection beads and capture probe signals using a detection module operable to capture one or more images of the one or more beads flowing within the fluidic chip. The methods and devices disclosed herein are compatible with a variety of sample preparation techniques used by skilled practitioners; accordingly, a variety of sample preparation methods and devices can be integrated and customized into the devices and methods disclosed herein, or can be separate from the devices and methods disclosed herein. In some embodiments of the methods described herein, the detection beads are fluorescent. In some embodiments of the methods described herein, the detection beads vary in fluorescent wavelengths. In some embodiments of the methods described herein, the detection beads vary in fluorescent intensities. In some embodiments of the methods described herein, the detection beads vary in size. In some embodiments of the methods described herein, the detection beads are coupled with a capture probe. In some embodiments of the methods described herein, the detection beads have a magnetic microbead core. In some embodiments of the methods described herein, the detection beads have a polymer coating. In some embodiments of the methods described herein, the detection beads have quantum dots. In some embodiments of the methods described herein, the capture probe is an antibody. In some embodiments of the methods described herein, the capture probe is an oligonucleotide probe. In some embodiments of the methods described herein, the detection molecule is biotinylated. In some embodiments of the methods described herein, the detection molecule can be detected with streptavidin conjugated with phycoerythrin.

In another aspect, disclosed herein are kits for assaying multiple antigens, analytes, or other microparticulates comprising: one or more multiplex bead array cartridges; one or more sterile lancets; and one or more sterile capillary tubes. In some embodiments, the kit may include cartridges containing microparticles conjugated to a capture probe, a detection molecule, and a fluorescent label. In some embodiments, the kit may include ancillary reagents such as, but not limited to, buffers, dilutants, washing agents, or other reagents required by the application. In some embodiments, the kit further comprises a detection module. In some embodiments, the kit may include calibration beads. In some embodiments, the kit's capillary tube is marked so as to ensure the correct amount of blood is collected and transferred to the disposable housing. In some embodiments, the kit's capillary tube is heparinized or EDTA coated.

The embodiments disclosed herein offer superior cost effectiveness, portability, and usability as compared to currently available technology. The multiplex detection and analysis system is rugged, portable and compact, allowing for accurate and sensitive analysis in the field.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
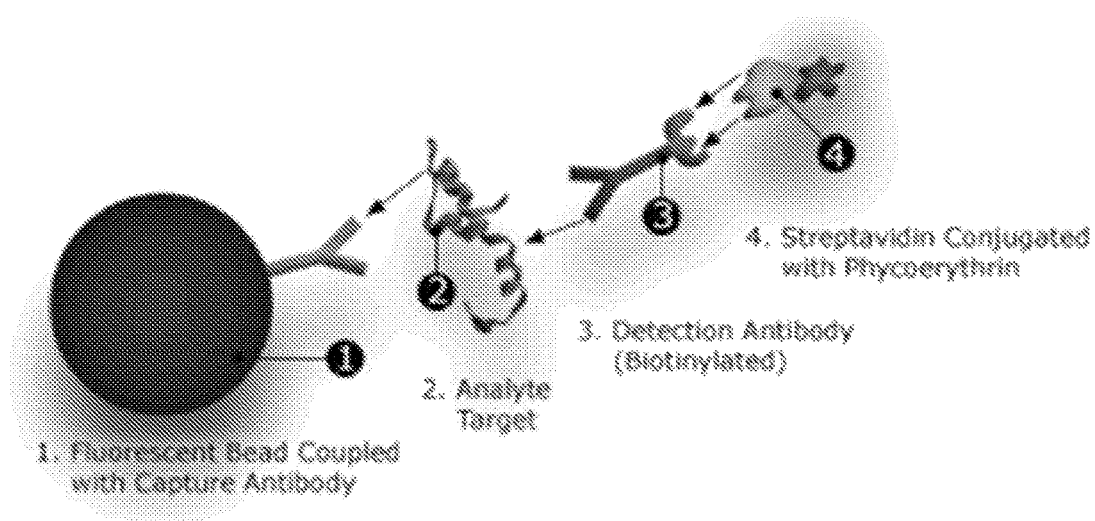
FIG. 1 shows a non-limiting example of a multiplex detection bead sandwich assay.
Figure 2A:
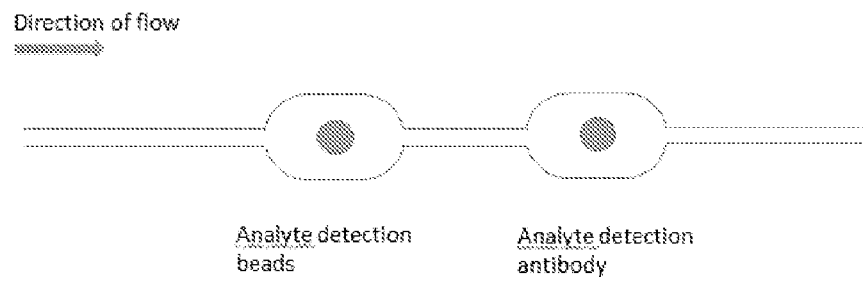
FIG. 2A-D shows a non-limiting example of (A) the assay components within the microfluidic chamber (B) the sample flowing through analyte detection beads (C) the sample flowing through analyte detection molecule (D) the detection bead/antibody complex flowing through the detection window.
Figure 2B:
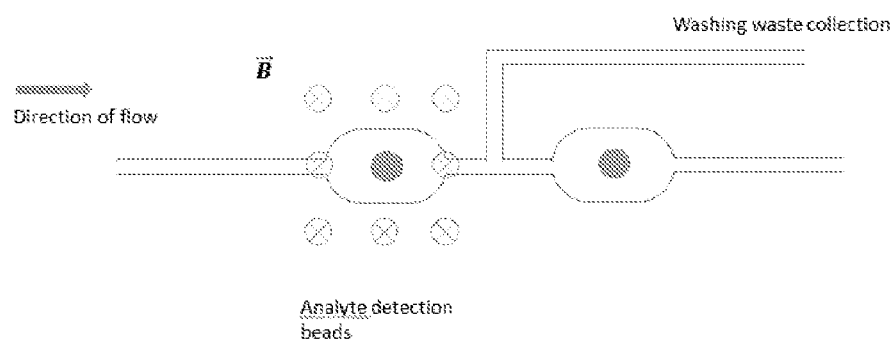
Figure 2C:
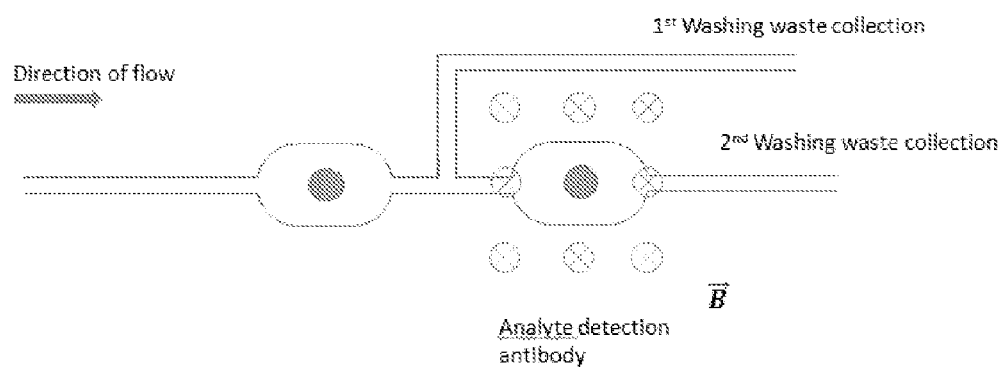
Figure 2D:
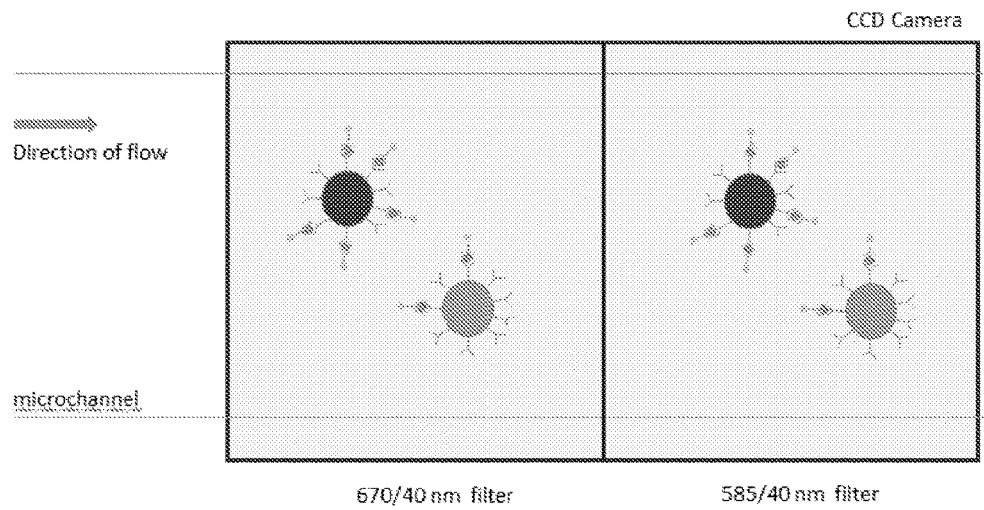

Flow cytometry is a technique used in the field of particle detection and identification. Typically, flow cytometer instruments require complex infrastructure and highly trained personnel. The use of flow cytometry in the clinic is limited due to the size and cost of such systems. Advantages of systems, methods, and kits, described herein include, but are not limited to, providing a simpler, more compact, cost effective, and portable particulate detection and analysis system. Further advantages of the cartridge, detection module, system, and kit described herein include having the sample flow over the detection module, which allows the detection module to remain in the same position, precluding necessary repositioning of a chip, sample, or filter. Still further advantages of the cartridge, detection module, system, and kit described herein include diminished clumping of particulates, scaling capabilities to analyze many different types of particulates, and continuous image capturing capabilities.

Described herein, in certain embodiments is a system for analyte, antigen, and microparticle detection and analysis comprising: one or more housing units; a cartridge containing a multiplex bead array located on a fluidic chip, the fluidic chip incorporating at least one microfluidic channel that one or more detection beads flow through within the fluidic chip; a detection window incorporated in one of the one or more housings, the detection window being operable to facilitate the capture of one or more images of one or more detection beads flowing within the detection window; and a detection module, the detection module comprising an optical imaging system and software for image analysis, that allows communication to and from a central database.

Also described herein, in certain embodiments are methods for detecting an analyte, antigen, and/or microparticle in a sample comprising: introducing a sample to a microfluidic chamber on a microfluidic chip; mixing the sample with detection beads; washing the sample and detection bead mixture; mixing the sample and detection bead mixture with a labelled capture molecule; washing the sample, detection bead, and detection molecule mixture; and detecting the detection beads and capture molecule using a detection module operable to capture one or more images of the one or more bound and unbound detection beads flowing within the fluidic chip.

Also described herein, in certain embodiments are kits, comprising: one or more multiplex bead array cartridges; one or more sterile lancets; and one or more sterile capillary tubes.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise noted.

Analysis

In some embodiments, the systems, methods, and kits described herein include assaying multiple cells, antigens, analytes, or other microparticulates. In further embodiments, "cell" or "cells" may include all types of cellular material, including but not limited to human cells, e.g., white blood cells, whole blood cells, lymphocytes and other cells derived from a human, animal cells, microbial cells, including but not limited to bacteria, fungal, or viral cells. In some embodiments, "microparticulates" may include all organic and inorganic particles and particulate matter, with different shapes, sizes, chemical and biological modifications, including but not limited to cellular debris, cell membranes, organelles, synthetic beads or particles, and other particles or particulates or combinations thereof. In further embodiments, the particles may include organic compounds such as, but not limited to, proteins, enzymes, metabolites, vitamins, toxins, carbohydrates and/or fats. In further embodiments, the particles may include a drug or other medicine. In further embodiments, the particles may include allergens, such as, but not limited to pollen, spores, dust, and dander. Other cells, antigens, analytes, or other microparticulates, or combinations thereof, known to those skilled in the art may also be used.

In further embodiments, the assay for multiple antigens, analytes, or other microparticulates described herein are operable to achieve white blood cell analysis. In some embodiments, the cell and particle sample detection and analysis devices and methods disclosed herein are operable to detect HIV, hepatitis B, hepatitis C, syphilis, sepsis, malaria and other indications or diseases. In other embodiments, the cell and particle sample detection and analysis devices and methods disclosed herein are capable of detecting food and water-borne pathogens. In yet other embodiments, the cell and particle sample detection and analysis devices and methods disclosed herein are capable of quantifying creatinine and viral load for HIV/AIDS. In still other embodiments, the cell detection and analysis devices and methods disclosed herein are operable to achieve CD4 T-cell analysis and counting. In further embodiments, the cell and particle sample detection and analysis devices, systems and methods described herein may be operable to achieve other types of analysis and counting, for example, such as analysis and counting of CD3, CD8, CD64, CD4 or CD45 cells. Also, in some embodiments, the cartridges, detection modules, systems, and kits described herein may be operable to be used for tracking and counting cells with sizes from about submicron to 100 microns in diameter. In various embodiments, the cells or particles may be less than 10, 20, 30, 40, 50, 60, 70, 80, 90, or 100 microns. In yet other embodiments, the cells or particles may be more than 1, 10, 20, 30, 40, 50, 60, 70, 80, 90 or 100 microns.

In some embodiments, the sample comprises bodily fluid, whole blood, blood, serum, plasma, cerebrospinal fluid, body tissue, urine or saliva, sputum, water, milk or other fluidic samples. In other embodiments, the sample is from a human, an animal, a plant, an insect, or a cell culture. In other embodiments, the sample is from a food, a beverage, a growth medium, an environmental sample, a liquid, water, or a combination thereof.

Housing Units

In some embodiments, the systems, methods, and kits described herein include a housing unit, or use of the same. In further embodiments, the housing unit is formed out of any suitable housing material, for example, but not limited to, a plastic or metal material, or combination of the same. In further embodiments, the size and shape of the housing may vary with the configuration of the cartridge.

Internal Quality Control and Intensity Calibration System

In some embodiments, the systems, methods, and kits described herein include an internal quality control and intensity calibration system, or use of the same. In further embodiments, the quality control and internal intensity calibration system may consist of commercially available beads. In still further embodiments, the quality control and internal intensity calibration system may include alignment beads, bead counting standards, compensation beads, performance tracking beads, reference beads, or size calibration beads. In some embodiments, the beads are coated with a dye, including but not limited to phycoerythrin (PE), PE-Cy5, PE-Cy7, Pacific blue, Cascade blue, Brilliant violet, APC, nanoparticles, gold nanoparticles, quantum dots and other suitable dyes or nanoparticles. In yet further embodiments, the internal intensity calibration system may include phycoerythrin (PE) (excitation/emission 532 nm/585 nm) and PE-Cy5 (excitation/emission 532 nm/700 nm) labelled beads, 6-8 microns in diameter. In alternative embodiments, the fluorescent dyes are injected into the beads. In some embodiments, the quality control and internal intensity calibration system may incorporate saline, for example, such as 1× phosphate-buffered saline (PBS). In further embodiments, the internal quality control and intensity calibration system may consist of control cells, such as, but not limited to immunotrol.

Detection Beads

In some embodiments, the systems, methods, and kits described herein include detection beads, or use of the same. In further embodiments, the detection beads may be microspheres. In further embodiments, the detection beads may be microparticles. In further embodiments, the detection beads are polystyrene-based microspheres. In further embodiments, the detection beads are polyethylene-based microspheres. In further embodiments, the detection beads may contain a magnetic microbead core, with a polymer coating. In further embodiments, the polymer coating may be, but is not limited to, polystyrene, or polystyrene in combination with other co-polymers such as polymethylmethacrylate (PMMA), divinylbenzene, polyvinyltoluene (PVT), styrene, butadiene, vinyltoluene, latex, or silica. In further embodiments, the detection beads may consist of commercially available beads. In further embodiments, the detection beads may be Dynabeads, nanoparticles, nanostrips, quantum dots, polymer beads embedded with quantum dots. In further embodiments, the detection beads may be 0.1 to 1,000 microns in diameter. The detection beads are preferably 1-100 microns in particle size. In further embodiments, the detection beads may be 1 to 10 microns in diameter. In yet further embodiments, the detection beads may be 6-8 microns in diameter. In further embodiments, the detection beads are coated with a dye, including, but not limit to phycoerythrin (PE), PE-Cy5, PE-Cy7, Pacific blue, Cascade blue, Brilliant violet, APC, nanoparticles, gold nanoparticles, quantum dots and other suitable dyes or nanoparticles. In alternative embodiments, a fluorescent dye may be injected into the beads. In further embodiments, the detection beads are conjugated to a capture probe. In further embodiments, the capture probe is an antibody. In further embodiments, the capture probe is a monoclonal antibody. In further embodiments, the capture probe is a polyclonal antibody. In further embodiments, the capture probe is an oligonucleotide probe. The methods disclosed herein are performed on a portable, or handheld, platform for point-of-care testing with a microfluidic chip system.

Detection Molecule

In some embodiments, the systems, methods, and kits described herein include detection molecules. In further embodiments, the detection molecules include a binding domain and a label domain. In further embodiments, the detection molecules are fluorescently labeled. In further embodiments, the fluorescent label may include, but is not limited to, Cy2, Cy3, Cy3B, Cy3.5, Cy5, Cy5.5, Cy7, carboxyfluorescein, fluorescein isothiocyanate, fluorescein amidite, hydroxycoumarin, aminocoumarin, methoxycoumarin, cascade blue, pacific blue, pacific orange, lucifer yellow, NBD, R-Phycoerythrin (PE), PE-Cy5 conjugates, PE-Cy7 conjugates, PE-Texas Red, PerCP, FluorX, BODIPY-FL, TRITC, X-Rhodamine, Texas Red, Allophycocyanin (APC), APC-Cy7 conjugates DyLight dyes, AlexaFluor dyes, ATTO dyes, or FluoProbes. In further embodiments, the fluorescent label may include, but is not limited to, Hoechst 33342, DAPI, Hoechst 33258, SYTOX Blue, Chromomycin A3, Mithramycin, YOYO-1 Ethidum Bromide, Acridine Orange, SYTOX Green, TOTO-1, TO-PRO-1, TO-PRO, Thiazole Orange, CyTRAK Organce, Propidium Iodide, LDS 751, 7-AAD, SYTOX Orange, TOT-3, TO-PRO-3, DRAQS, or DRAQ7. In further embodiments, the fluorescent label may include, but is not limited to, GFP (Y66H mutation), GFP (Y66F mutation), EBFP, EBFP2, Azurite, GFPuv, T-Sapphire, Cerulean, mCFP, mTurquoise2, ECFP, CyPet, GFP (Y66W mutation), mKeima-Red, TagCFP, AMCyanl, mTFP1, GFP (S65A mutation), Midoriishi Cyan, wild type GFP, GFP (S65C mutation), TurboGFP, TagGFP, GFP (S65L mutation), EGFP, Azami Green, ZsGreenl, TagYFP, EYFP, Topax, Venus, mCitrine, YPet, TurboYFP, ZsYellow1, Kusabira Orange, mOrange, mKO, TurboRFP, tdTomato, TagRFP, DsRed monomer DsRed2, mStrawberry, TurboFP602, AsRed2, mRFP1, J-Red, R-phycoerythrin (RPE), B-phycoerythrin (BPE), mCherry, HcRed1, Katusha, P3, Peridinin Chlorophyll, mKate (TagFP635), mPlum, or mRaspberry. Other fluorophores or combinations thereof known to those skilled in the art may also be used.

Fluidic Chip

In some embodiments, the systems, methods, and kits described herein include fluidic chip, or use of the same. In further embodiments, the fluidic chip may be a fluidic cartridge, a microfluidic cartridge, a fluidic cartridge, a microfluidic cartridge, a microfluidic chip, or some other applicable element. In yet further embodiments, the fluidic chip may contain a base layer, a second layer, and a capping layer. Is other embodiments, the fluidic chip may contain a base and capping layer. In some embodiments, the base layer may incorporate fluidic structures, for example, but not limited to, structures defined in a SU-8 negative photoresist, plastic, acrylic or polymer material. In further embodiments, the fluidic channels may be patterned using a photolithography technique such that the depositing step may involve spin coating and drying techniques, or hot embossing/injection moulding. In other embodiments, the base layer may have lengths ranging from 1 to 300 mm and width ranging from 1 to 200 mm. In some embodiments, the base layer may comprise glass, polymer, metal, semiconductor material, such as silicon, or combinations of the same. In yet further embodiments, the base layer may be fully cured. In some embodiments, the second layer may be deposited by the same steps as used to deposit the base layer. In further embodiments, the second layer may be further patterned, such as, but not limited to, exposing through a photomask. In some embodiments, the second layer may have lengths ranging from 1 to 300 mm, and width ranging from 1-200 mm. The other embodiments, the second layer may comprise glass, polymer, photoresist, or mixtures thereof. In some embodiments, the capping layer may be made of a variety of materials, such as, but not limited to plastic acrylic. In further embodiments, the capping layer may be partially cured SU-8 photoresist layer deposited with mechanically drilled holes to form inlets and outlets. In some embodiments, a housing is included to protect the fluidic cartridge. In other embodiments, the housing may be made from polymer material, such as plastic acrylic, using an injection moulding process. In some embodiments, the housing also allows ease of use for the user to handle the cartridge.

In some embodiments, the fluidic chip may incorporate one or more areas, such as a sample loading compartment, a mixing chamber, a reaction chamber, a fluidic channel, an analysis chamber, and a waste collection chamber. In further embodiments, the fluidic chip may contain a sample loading compartment, where the sample is transferred by pipette into a port. In further embodiments, the sample loading compartment is treated with EDTA. In some embodiments, the cartridge accommodates a blood sample, for example from a finger prick collected using a pipette. In some embodiments, from about 1 to about 100 microliters, from about 1 to about 50 microliters, from about 1 to about 25 microliters, from about 1 microliters, from about 5 microliters, from about 10 microliters, from about 15 microliters, from about 20 microliters, from about 25 microliters, from about 30 microliters, from about 35 microliters, from about 40 microliters, from about 45 microliters, from about 50 microliters, from about 55 microliters, from about 60 microliters, from about 65 microliters, from about 70 microliters, from about 75 microliters, from about 80 microliters, from about 85 microliters, from about 90 microliters, from about 95 microliters, from about 100 microliters will be transferred to the microfluidic cartridge using the pipette. In another embodiment, the microfluidic cartridge can have a sample collection port where a blood sample, for example from a finger prick, can be directly collected and loaded on to the cartridge.

In yet further embodiments, the sample loading compartment requires a cap, plug, or seal. In some embodiments, the sample loading compartment comprises a cap, plug or seal as disclosed in PCT/EP2014/064290, which is incorporated in its entirety herein. In still further embodiments, the sample loading compartment is hermitically sealed. In still other embodiments, the fluidic chip may contain a mixing chamber, where the sample may be mixed with reagents. In yet other embodiments, the mixing chamber may contain slow-dried or freeze dried reagents. In further embodiments, the reagents are lyophilized. In still other embodiments, the cap, plug, or seal may be coated with or contain reagents for mixing in situ within the cartridge. In yet further embodiments, the mixing chamber may contain fluorescently labelled antibodies. In some embodiments, the mixing chamber may contain antibodies coated onto beads. In yet other embodiments, the antibodies coated onto beads may be fluorescently labeled. In yet further embodiments, the mixing chamber is a passive fluidic mixer and may be contained within the preparation chamber or analysis chamber. In still further embodiments, the fluid within the mixing chamber may be mixed using a bellows-actuated system. Because of the ability to multiplex with the methods and devices herein, more than two samples may be mixed together to perform the detection methods disclosed herein.

In some embodiments, the fluidic chip may contain a fluidic channel or multiple microfluidic channels, where the channel may include a narrow interrogation region that may be designed to create a laminar flow of cells or particles. In further embodiments, the fluidic chip may contain a plurality of microfluidic channels. In some embodiments, the fluidic channel interrogation region may be may be less than 1500 microns, less than 1200, less than 900 microns, less than 800 microns, less than 700 microns, less than 600 microns, less than 500 microns, less than 400 microns, less than 300 microns, less than 200 microns, or less than 100 microns wide. In other embodiments, the fluidic channel interrogation region may be from about 400 microns to about 1000 microns wide. In yet other embodiments, the fluidic channel interrogation region may be from about 500 to about 700 microns wide. In still other embodiments, the fluidic channel interrogation region may be 100 to 1000 microns wide. In some embodiments, the fluidic channel interrogation region may be 600 microns wide. In other embodiments, the fluidic channel interrogation region may be less than 2000 microns, less than 1800 microns, less than 1600 microns, less than 1500 microns, less than 1400 microns, less than 1300 microns, less than 1200 microns, less than 1100 microns, less than 1000 microns, less than 800 microns, less than 600 microns long. In some embodiments, the fluidic channel interrogation region may be from about 800 to about 1600 microns long. In still other embodiments, the fluidic channel interrogation region may be from about 1000 to about 1400 microns long. In further embodiments, the interrogation region may be approximately 1-50 microns, less than 10 microns, less than 20 microns, less than 30 microns, less than 40 microns, or less than 50 microns deep. In yet further embodiments, the interrogation region may be greater than 10 microns, greater than 20 microns, greater than 30 microns, greater than 40 microns, or greater than 50 microns deep. In yet further embodiments, the fluidic channel interrogation region. In further embodiments, the interrogation region may be defined by the size of the detection module.

In some embodiments, the microfluidic channel may include one or more posts. In further embodiments, the microfluidic channel posts may be a variety of sizes and/or in a variety of shapes, including but limited to a square, a circle, a rectangle or a hexagon. In some embodiments, the posts could be glass, polymer, photoresist or combinations thereof. In other embodiments, the microfluidic channel posts may be positioned at regular, uniform intervals within the channel, or may be randomly spaced. In further embodiments, the posts may be 1-200 microns in width, including posts less than 10, 20, 30, 40, 50, 60, 70, 80, 90, 100, 110, 120, 130, 140, 150, 160, 170, 180, 190, or 200 microns wide, including any width therein. In yet further embodiments, the posts may be may be more than 1, 10, 20, 30, 40, 50, 60, 70, 80, 90, 100, 110, 120, 130, 140, 150, 160, 170, 180, 190, or 200 microns wide, including any width therein. The posts may be of different heights to separate layers of the chip. The posts may be used to keep the cells or particles from clumping. In some embodiments, the posts are used to separate cell or particulate sizes, and/or to drive fluid flow in the fluidic and mixing channel.

In some embodiments, the microfluidic channel may be a patterned channel. In further embodiments, the pattern may be a curved pattern. In further embodiments, the pattern may be a straight pattern. In further embodiments, the pattern may be a serpentine pattern. In further embodiments, the pattern may be a meandering pattern. In further embodiments, the pattern may be a "u" pattern. In further embodiments, the pattern may be a "w" pattern. In further embodiments, the pattern may be a "c" pattern. In further embodiments, the pattern may be a microvascular pattern. In further embodiments, the pattern may be a zigzag pattern. In further embodiments, the patter may be a geometric pattern.

In some embodiments, the microfluidic channel may take the form of various geometrical or patterned shapes. In further embodiments, the microfluidic channel may be a cylindrical channel. In further embodiments, the microfluidic channel may be oval. In further embodiments, the microfluidic channel may be triangular. In further embodiments, the microfluidic channel may be square. In further embodiments, the microfluidic channel may be rectangular. In further embodiments, the microfluidic channel may be spindle-shaped. In further embodiments, the microfluidic channel may be an irregularly shaped. In further embodiments, the microfluidic channel may be custom shaped. In further embodiments, the microfluidic channel may be "v" shaped.

In some embodiments, the microfluidic channel system may take the form of meandering serpentine structures. In further embodiments, sample is actuated back and forth in a reagent chamber. In further embodiments, the meandering serpentine structures, both upstream and downstream to the reagent chamber, enhance the mixing between sample and on-chip reagent. In further embodiments, the reagent is dried and integrated into the cartridge during assembly process. In yet further embodiments, the reagent is in liquid form and introduced into the cartridge during the test preparation procedure.

In some embodiments, the fluidic chip may contain an analysis chamber, where the sample moves into and fills up the analysis chamber. In further embodiments, sample entry into the analysis chamber may be filled once the entire sample has entered the analysis chamber, or before the sample has entered the analysis chamber. In further embodiments, the analysis chamber may trigger the optical detector in the detection module to start capturing images. In yet further embodiments, once the entire analysis chamber is completely filled, the optical detector's image capturing process may stop and the captured images may then be combined for analysis.

In some embodiments, the fluidic chip may include a sample introduction inlet, a sample preparation chamber, a reagent chamber, an antigen, analyte, or other microparticulate analysis chamber, a detection window, and a waste reservoir. In further embodiments, the inlets and chambers are connected so that the introduction inlet is connected to the preparation chamber, so that cells or particles introduced to the cartridge may flow from the introduction inlet through the preparation chamber to the analysis chamber and through the analysis chamber to the waste reservoir. In yet other embodiments, the waste reservoir may be incorporated as disclosed in EP2437890, which is incorporated herein in its entirety. In still further embodiments, the waste chamber is connected to the preparation chamber. In yet further embodiments, the cells or particles collected in the waste reservoir may be disposed of through removal of the waste reservoir. In still further embodiments, the waste reservoir is reattachable. In further embodiments, the waste reservoir may contain a disposable container. In still further embodiments, the waste reservoir itself is disposable. In still further embodiments, the cells or particles may be removed from the waste reservoir without detaching the waste reservoir, for example, but not limited to, flushing or aspiration of the sample.

In some embodiments, the flow of fluid within the fluidic chip may be driven by capillary force. In further embodiments, the flow of fluid within the fluidic chip may be driven by pressure variation due to actuator volume change. In further embodiments, the flow of fluid within the fluidic chip may be a laminar flow. In further embodiments, the fluidic chip may be disposable. In still further embodiments, the fluidic chip may be made of glass or polymer substrates, such as, but not limited to, plastic acrylic. In yet further embodiments, the fluidic chip may be made from hot embossing or injection molding techniques. In some embodiments, the fluidic chip may be fabricated using a photolithography technique.

Detection Window

In some embodiments, the systems, methods, and kits described herein include a detection window, or use of the same. In further embodiments, the detection window allows for the optical detector to capture images of cells or particles flowing into or through the analysis chamber. In yet further embodiments, the detection window may be coated with one or more optical filters; here, the optical filters may be adhered to the top surface of the detection window or the coating may be provided on an independent transparent optical element that may be positioned in front of the window section, or the filters are placed in front of the detector. In some embodiments, the detection window is divided into one or more sub regions for multi-wavelength fluorescence detection. In some embodiments, the transparent window may be made from material with excellent optical properties such as transparent polymer, or glass. In other embodiments, there is no magnification factor associated with the filters. In yet other embodiments, the filter is a fluorescence emission filter. In some embodiments, the ranges of the emission filters are 585/40 nm, 670/40 nm, 650 long pass filter, or 708/75 nm. In some embodiments, the detection window may be positioned under, over, or upon a portion of the disposable cartridge, or under, over, or upon the whole of the cartridge. In still further embodiments, the detection window may incorporate the same color optical filter two or more times. This may be used to calculate an average as the cell sample passes by the detection window. In a further embodiment, the detection channel can pass through the detection window.

Detection Module and Optical Detector

In some embodiments, the systems, methods, and kits described herein include a detection module, or use of the same. In further embodiments, the detection module may include an optical imaging system and software for image analysis.

Optical Source

In some embodiments, the systems, methods, and kits described herein include an optical source, or use of the same. In further embodiments, the optical source may be a light illuminating source. In some embodiments, the light illuminating source may be a laser diode or light emitting diode device. In still further embodiments, the light source may be a fiber optic light source. In further embodiments, the fiber optic light source may include a light guide. In still further embodiments, the optical source may be a free space or fiber/light guide coupled with or otherwise connected to the optical source. In further embodiments, the light source may be a semiconductor based laser device. Including but not limited to vertical-cavity surface-emitting laser (VCSEL). In yet further embodiments, the optical source may be, located above or below the cartridge, but is not limited to these two locations. In some embodiments, the optical source may also include a free space optical filter and/or a Bragg grating filter that may be integrated in the fiber/light guide. In further embodiments, the optical source may include an optical detector. In yet further embodiments, the optic light delivery may be coated with an excitation filter.

Optical Detector

In further embodiments, the detection module may be an image acquisition and analysis module that may include an optical detector. In still further embodiments, the optical detector may be a variety of types, for example, an array of photodiodes, a photomultiplier tube, a charge coupled device (CCD) image sensor, or a complementary metal oxide semi-conductor (CMOS) image sensor. In further embodiments, the CCD or CMOS sensor may have an active sensing area diagonal width of 0.5 mm or less, 1 mm or less, 2 mm or less, 3 mm or less, 4 mm or less, 5 mm or less, 6 mm or less, 7 mm or less, 8 mm or less, 9 mm or less, 10 mm or less, 15 mm or less, 20 mm or less, 30 mm or less, 40 mm or less, 50 mm or less, 60 mm or less, 70 mm or less, 80 mm or less, 90 mm or less or 100 mm or less. In still further embodiments, the CCD or CMOS sensor. In yet further embodiments, a CCD sensor may take the dimensions of a 3 mm×0.5 mm rectangular sensor, or the CCD sensor may have an active detection area of approximately 10.2 mm×8.3 mm. In yet further embodiments, the CCD sensor may be, but is not limited to, a CCD camera. In some embodiments, the optical detector may capture optical images over time, at regular or irregular intervals. In some embodiments, the optical detector is coated with one or more emission filters, where the coating may be a direct coating, or an independent optical element that may be positioned in front of the window section of a fluidic chip. In still further embodiments, the optical detector may incorporate fluorescence filters in a single cell. In some embodiments, the filter shape is a circle, half-moon shaped, rectangle or square. In some embodiments, the detection region is separated into two sub regions to detect fluorescence. In some embodiments, the detection region is divided into one or more sub regions for multi-wavelength fluorescence detection. In further embodiments, the optical detector may not include either an emission filter or any dichroic mirrors. In still further embodiments, the optical detector may contain optical filters for fluorescence emission collection, including, but not limited to, broad band, 585/40, 670/40 and 708/75 filters. In further embodiments, the optical detector may contain a custom designed emission filter. In further embodiments, the optical detector may be further divided up into a number of small sub-regions, and each sub-region may be coated with an optical filter. In further embodiments, each sub-region may detect or otherwise highlight one particular color or fluorochrome, as a result of the optical filter. In yet further embodiments, two or more independent fluorescence images may be superimposed, to create a multi-color fluorescence cytometry system.

Lens

In some embodiments, the optical imaging system may include a lens. In further embodiments, the lens is a magnification lens, for example a three element telescopic 5×, 7×, 10×, 20× or other suitable optical lenses, or other lens. In still further embodiments, the lens is an off-the-shelf microscope objective lens. In still further embodiments, the lens may be a microscope objective lens, such as, but not limited to, 4× NA 0.1 objective lens, a 10× NA 0.25 objective lens, a 10× NA 0.30 objective lens, or other suitable objective lens configuration. In yet further embodiments, the lens may be positioned above or below a disposable cartridge. In further embodiments, the lens may be an optical lens tube assembly. The magnification lens may magnify the targeted cells or particles and may project these cells or particles onto an optical detector.

Software

In some embodiments, the systems, methods, and kits described herein include software, or use of the same. In further embodiments, the software may be an image analysis program. In further embodiments, the image analysis program may utilize the images captured by the optical detector. In further embodiments, the image analysis program may be used to detect intensity levels in the samples. In further embodiments, the image analysis program may be used to analyze and process the acquired optical images for particle and cell detection, tracking, and enumeration. In further embodiments, the image analysis program includes an algorithm, and the algorithm may be applied to any number of characteristics, including, but not limited to, motion analysis of cells or particles flowing through the detection window, or statistical data of the entire sample. In still further embodiments, the image analysis program includes a two-phase analysis, by which the first step includes collecting a set of images generated during a specified time period and the second step includes collecting and analyzing the images as a group. In yet further embodiments, image analysis occurs in real time, as the cells or particles pass through the detection window; in this embodiment it is not necessary to collect a set of images before beginning an analysis step. In some embodiments, the image analysis program is configured to achieve.

Networking Modules

In some embodiments, the apparatuses, platforms, devices, systems, methods, media, and software described herein include one or more networking modules, or use of the same. In some embodiments, the network module is part of the apparatus/platform/system/device, or is coupled with the apparatus/platform/system/device. The network module is wireless. The wireless module comprises a cellular interface, or a non-cellular interface, or a combination of cellular interface and non-cellular interface. In certain embodiments, the networking module operates on satellite communication and/or global positioning system (GPS). People with skills in the art can easily recognize various protocols running on the network; non-limiting examples include: the Internet protocol, TCP protocol, FTP, UDP, XML, and data binding scheme like XSD.

In some embodiments, the networking module comprises an electronic logic specifically designed for transmitting the data (e.g., test results, patient profiles, height, weight, diary information, and pictures taken at the point-of-care site). In some embodiments, the networking module is a portable digital processing device (e.g., smartphones, tablets, portable computers, laptops, desktops, all-in-one computers, palm computers, etc) coupled with the apparatus/platform/system/device for data transmission.

In some embodiments, the networking module comprises an electronic logic specifically designed for transmitting the data (e.g., test results, patient profiles, height, weight, diary information, and pictures taken at the point-of-care site). In some embodiments, the networking module is a portable digital processing device (e.g., smartphones, tablets, portable computers, laptops, desktops, all-in-one computers, palm computers, etc) coupled with the apparatus/platform/system/device for data transmission.

Data Encryption and Protection

In some embodiments, one or more data encryption mechanisms are employed. In some embodiments, a data encryption mechanism is used to comply with the HIPAA standard. In some embodiments, a data encryption mechanism is used to comply with a regulation requirement. In some embodiments, a software module with an encryption protocol is applied before the networking module/interface sends out the data. In some embodiments, a network module/interface encrypts data packets before sending out the data packets. In some embodiments, an encryption software module is adopted at a receiver to decrypt the encrypted data. In some embodiments, the networking module/interface at the receiver decrypts encrypted data packets upon receiving them. Non-limiting examples of the encryption algorithms include cryptographically secure pseudorandom number generators, information-theoretically secure algorithms, integer factorization algorithms, primality tests, symmetric-key algorithms, advanced access content system, symmetric-key algorithms, broken cryptography algorithms, cryptanalytic algorithms, SHA algorithms, RSA algorithms, and cryptographic hash functions. Encryption may utilize the key pair concept that utilizes a public key, private key and/or passphrase (as is used in secure email transfer). For example, whenever the sender wishes to send an encrypted sequence, they must have the recipient's public key. Similarly, the receiver must also have the sender's public key. A private key is connected to exactly one public key. Without a private key, the content of the encrypted data is extremely difficult to extract. A key length of 80 bits is generally considered the minimum for strong security with symmetric encryption algorithms. However, a person skilled in the art easily recognizes the number of bits in an embodiment. Frequently, 128-bit keys are used and considered very strong. A keyed-hash message authentication code (HMAC) may also be used to generate a message authentication code using a cryptographic hash function in combination with a secret cryptographic key. The message authentication code may be used simultaneously to verify both the data integrity and authenticate the sequence or data being sent. Keys for sending and receiving sequence data may be generated truly randomly and contain sufficient entropy. Entropy can be derived from unpredictable computer operations such as the movement of a disk drive head.

In some designs, encryption comprises a key exchange mechanism. Non-limiting examples of the key exchange information includes, but not limited to, public key infrastructure (PKI), transfer of PKI certificates, symmetric key information, asynchronous key information and any key negotiation information between nodes that exchange encrypted information. A person with skill in the art can easily recognize possible embodiments of encryption key exchange.

In some embodiments, when encrypted data is to be transmitted, the transmission comprises one or more pieces of encryption information, such as an encryption key, a primitive, a seed, a protocol, an algorithm, an object, a program, a procedure, and others. A person with skill in the art can easily recognize encryption information being included.

In some embodiments, a communication channel is encrypted; an encryption key to be used to encrypt the channel should be prearranged or exchanged using an out-of-band and out-of-channel method. Data transmitted on such a communication channel may be plain texts or encrypted data.

In some embodiments, multiple layers of encryption are performed. For example, plain text data is encrypted by a first encryption mechanism; then, the encrypted data is further encrypted by one or more encryption mechanisms.

Digital Processing Device

In some embodiments, the apparatuses, platforms, devices, systems, methods, media, and software described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the descriptions disclosed herein, suitable digital processing devices include, by way of non-limiting examples, server computers, desktop computers, laptop computers, notebook computers, sub-notebook computers, netbook computers, netpad computers, set-top computers, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display is a cathode ray tube (CRT). In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In other embodiments, the display is e-ink or e-paper based. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera to capture motion or visual input. In still further embodiments, the input device is a combination of devices such as those disclosed herein.

Non-transitory Computer Readable Storage Medium

In some embodiments, the platforms, systems, software applications, media, and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Web Application

In some embodiments, a computer program includes a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, systems, software applications, media, and methods disclosed herein include software, server, and/or database modules, or use of the same. In view of the disclosure provided herein, software modules are created by techniques known to those of skill in the art using known machines, software, and languages. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

In some embodiments, the platforms, systems, software applications, media, and methods disclosed herein include one or more databases, or use of the same. In view of the disclosure provided herein, those of skill in the art will recognize that many databases are suitable for storage and retrieval of network event data. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

Example 1—Multiplex Bead Array Assay Components

Figure 3:
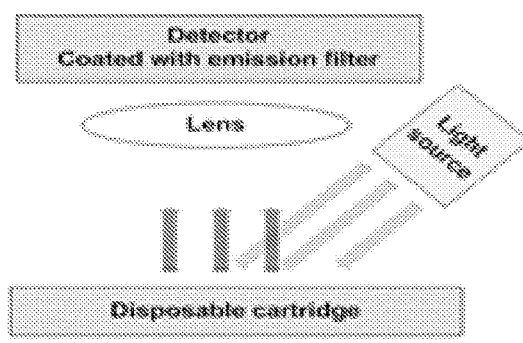
FIG. 3 shows a non-limiting example of an optical imaging system configuration.

FIG. 1 shows a non-limiting example of a multiplex detection bead sandwich assay. A mixture of beads are impregnated with different fluorescent or other light-based signals that allow differentiation of different populations of beads. Each fluorescent bead is coupled to a capture probe, which specifically binds to a portion of the target analyte. A detection molecule binds to a second, specific portion of the target analyte. In some cases the detection molecule is a biotinylated antibody, where streptavidin conjugated phycoerythrin then binds to the detection molecule. In other embodiments, the detection molecule is fluorescently labeled. The sample is exposed to multiple populations of beads, each containing unique capture probes directed to specific antigens or analytes, during the same assay, increasing the cost, efficiency, portability, and usability for point-of-care testing. FIG. 3 shows a non-limiting example of an optical imaging system configuration.

Example 2—Bead Flow Through Microfluidic Chamber

FIG. 2 shows a non-limiting example of (A) the assay components within the microfluidic chamber, (B) the sample flowing through a mixture of analyte detection beads, (C) the sample flowing through analyte detection probe, (D) the detection bead/antibody complex flowing through the detection window.

Example 3—Analysis of Target Detection

Figure 4:
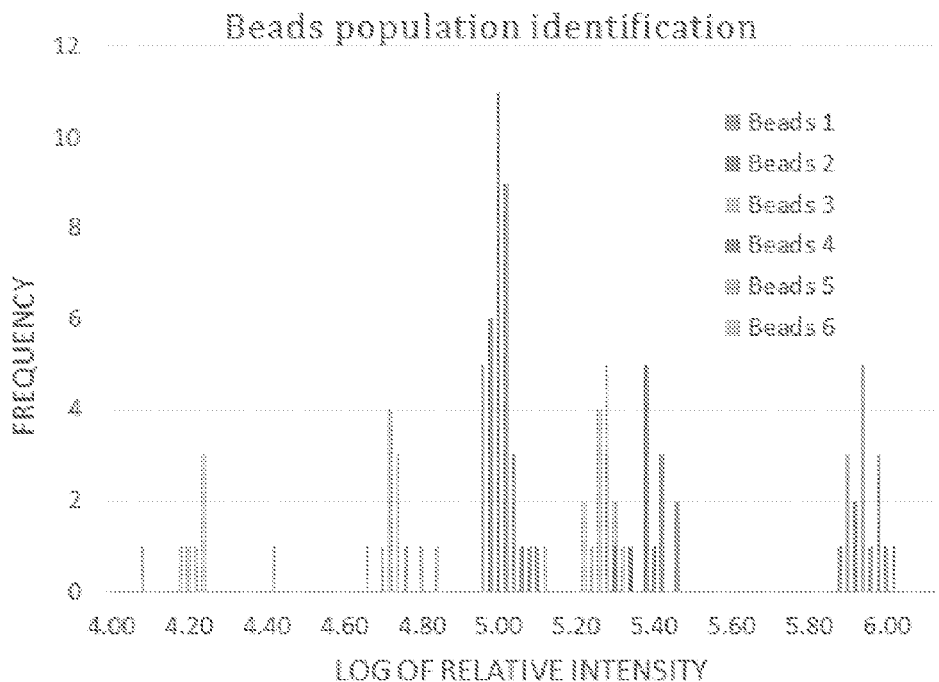
FIG. 4 shows a non-limiting example of bead population analysis based on the fluorescence intensity of the of the detection beads.
Figure 5:
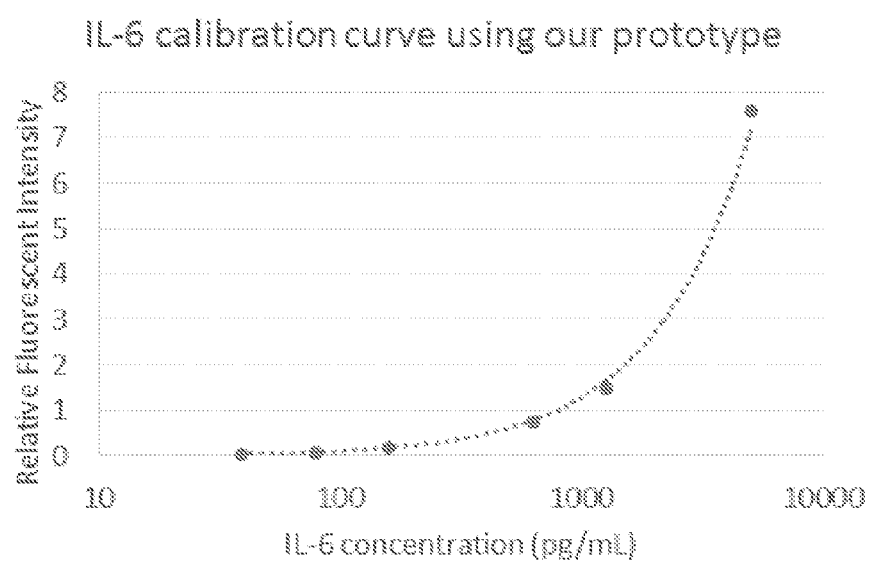
FIG. 5 shows a non-limiting example of calculating analyte concentration from the measured fluorescence intensity of the detection beads.

A user performs a multiplex bead array assay. The optical imaging system and software exhibits multiplexing capabilities, generating statistics of multiple individual analytes within a single sample. As an example, the user may analyze the data using a fluorescence filter or an arrayed filter in front of the optical detector. Images captured by the optical imaging system and displayed through the image analysis software, show detection of the sample as captured by the streptavidin conjugated phycoerythrin. FIG. 4 shows a non-limiting example of target analyte detection analysis. Six fluorescent beads of different fluorescent intensities are imaged, and the bead populations are separated by fluorescence intensity units. The amount of target analyte binding per bead population is quantified and shown as the number of beads bound by the detection probe per bead population. FIG. 5 shows a non-limiting example of target analyte quantification. The analyte concentration determines the amount of analyte bound to the fluorescent beads via fluorescently labeled capture antibody/antigen. The fluorescence intensity of the capture probe is a measure of the target analyte concentration in the sample. By generating a standard curve shown in FIG. 5, target analyte concentration in the sample can be determined.

Example 4—Mobile Health Provider

The system and device disclosed herein were served as a portable point-of-care assistance. Due to high mobility, a nurse is able to easily carry the device to visit various nursing homes. In a morning during a flu season, the nurse could visit a senior patient. The nurse could perform multiple tests to diagnose the flu status. The nurse could collect a single small blood drop, and the point-of-care device could analyze the infection status. The data is sent to a remote server, which is further accessed by a physician to real-time evaluate the results of the test. When a skeptical result is found, the physician could immediately call the nurse to provide appropriate care for the patient. The whole process takes no longer than 2 hours.

Due to portability, the nurse could further visit another patient in another town. The second patient has limited mobility, so it is more convenient for a nurse to visit his home rather than having the man visiting a clinic. The man requires was a regular physical checkup. The nurse utilizes the device disclosed herein to collect a single blood drop from the man, and the device could automatically identify the current health status of the man.

Our diagnostic and patient management platform is extremely mobile, simple to use, and inexpensive. From single drops of blood, health workers in remote locations can rapidly and accurately perform tests to diagnose or monitor a range of infectious and non-communicable diseases. Cloud connectivity enables the review of results from a central location for quality control, decision-making support, and facilitates EMR data aggregation.

What is claimed is:

1. A method for assaying at least two unique antigens, analytes, or other microparticulates, comprising:
    a) introducing a sample to a microfluidic chamber on a fluidic chip;
    b) mixing the sample with analyte detection beads to generate a sample and detection bead mixture in the fluidic chip, the detection beads comprising a mixture of beads impregnated with different fluorescent or other light-based signals that allow differentiation of different populations of beads, wherein at least two different capture probes, each capable of capturing a unique antigen, analyte, or other microparticulate are coupled to the detection beads;
    c) washing the sample and detection bead mixture in the fluidic chip;
    d) mixing the sample and detection bead mixture with at least two first detection molecules in the fluidic chip to generate a sample, detection bead, and first detection molecule mixture, wherein each of the first detection molecules comprise a binding domain and a label domain, and wherein the binding domain of each first detection molecule is capable of binding to the same unique antigen, analyte, or other microparticulate captured by the at least two different capture probes in step (b);
    e) washing the sample, detection bead, and first detection molecule mixture in the fluidic chip;
    f) mixing the sample, detection bead, and first detection molecule mixture with a second detection molecule in the fluidic chip, wherein the second detection molecule binds to the label domain of the first detection molecules in step (d), and comprises a fluorescent or other light-based signal marker, and wherein binding of the first and second detection molecules allows differentiation of detection beads bound to the unique antigens, analytes or other microparticulates in the sample and unbound detection beads;
    g) detecting the detection beads and first and second detection molecules in the fluidic chip using a detection module operable to capture one or more images of and distinguish the labels of the detection beads and first and second detection molecules flowing through the fluidic chip; and
    h) capturing sequential images of the unbound and/or bound detection beads using the detection module as the detection beads flow through the fluidic chip.

2. The method of claim 1, wherein the detection beads are fluorescent, wherein the detection beads vary in fluorescent wavelengths.

3. The method of claim 2, wherein the detection beads comprise a magnetic microbead core.

4. The method of claim 2, wherein the detection beads comprise quantum dots.

5. The method of claim 1, wherein the capture probes comprise an antibody or antigen.

6. The method of claim 1, wherein the capture probes comprise an oligonucleotide probe.

7. The method of claim 1, wherein the detection module incorporates an image analysis program operable to analyze the one or more images captured by the detection module to produce analysis results, wherein the analysis results are used to produce diagnostic results.

8. The method of claim 1, wherein the detection beads vary in signal intensity.

9. The method of claim 1, wherein the detection beads vary in size.

10. The method of claim 1, wherein the fluidic chip comprises a detection window that is divided into one or more sub-regions for multi-wavelength fluorescence detection.

11. The method of claim 1, wherein the detection module comprises a detection region that is divided into one or more sub-regions for multi-wavelength fluorescence detection.

12. The method of claim 1, wherein two or more captured images are superimposed to create a multi-color fluorescence image for analysis.

* * * * *